US010441265B2

(12) United States Patent  
Pasquali et al.

(10) Patent No.: US 10,441,265 B2  
(45) Date of Patent: Oct. 15, 2019

(54) ADJUSTABLE GRAFT FIXATION DEVICE

(71) Applicant: Medos International Sàrl, Le Locle (CH)

(72) Inventors: Meghan A. Pasquali, Providence, RI (US); Adam C. Gustafson, Dighton, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 247 days.

(21) Appl. No.: 15/665,585

(22) Filed: Aug. 1, 2017

(65) Prior Publication Data

US 2017/0325805 A1 Nov. 16, 2017

Related U.S. Application Data

(62) Division of application No. 14/340,683, filed on Jul. 25, 2014, now Pat. No. 9,757,113.

(Continued)

(51) Int. Cl.
| | |
|---|---|
| *A61B 17/04* | (2006.01) |
| *A61B 17/06* | (2006.01) |
| *A61F 2/08* | (2006.01) |

(52) U.S. Cl.  
CPC .... *A61B 17/0401* (2013.01); *A61B 17/06166* (2013.01); *A61F 2/0811* (2013.01);

(Continued)

(58) Field of Classification Search  
CPC ........ A61B 17/0401; A61B 2017/0404; A61B 2017/0475; A61B 17/06166;

(Continued)

(56) References Cited

U.S. PATENT DOCUMENTS

| 2,600,395 A | 6/1952 | Domoj et al. |
| 4,093,292 A | 6/1978 | Marcet et al. |

(Continued)

FOREIGN PATENT DOCUMENTS

| CN | 101170966 A | 4/2008 |
| CN | 102438548 A | 5/2012 |

(Continued)

OTHER PUBLICATIONS

EP Search Report for Application 14179156.6 dated Nov. 11, 2014 (8 pages).

(Continued)

*Primary Examiner* — Katherine M Shi

(57) ABSTRACT

Systems and methods for securing a soft tissue graft to bone are provided herein. In one embodiment, a surgical implant can include an elongate body having a longitudinal axis extending therealong and having first and second through-holes that are offset to a first side of the longitudinal axis and a third through-hole that is offset to a second side of the longitudinal axis and that is positioned between the first and second through-holes. The implant can also include a suture length extending through the first, second, and third through-holes such that a self-locking knot is formed on a first side of the body and a plurality of suture loops are formed on a second side of the body opposite the first side.

11 Claims, 15 Drawing Sheets

Related U.S. Application Data

(60) Provisional application No. 61/860,680, filed on Jul. 31, 2013.

(52) U.S. Cl.
CPC ........... A61B 2017/0404 (2013.01); A61B 2017/0414 (2013.01); A61B 2017/0459 (2013.01); A61B 2017/0475 (2013.01); A61F 2002/0852 (2013.01); A61F 2002/0882 (2013.01)

(58) Field of Classification Search
CPC .... A61B 2017/0458; A61B 2017/0459; A61B 2017/06185; A61B 17/0487; A61B 2017/0414; A61B 2017/0496; A61F 2002/0852; A61F 2002/0882; A61F 2/0811; A61F 2002/0823
USPC .................................. 606/148, 145, 228, 232
See application file for complete search history.

(56) References Cited

U.S. PATENT DOCUMENTS

| | | |
|---|---|---|
| 4,105,349 A | 8/1978 | Kupperman et al. |
| 4,133,604 A | 1/1979 | Fuller |
| 4,186,921 A | 2/1980 | Fox |
| 4,233,917 A | 11/1980 | Carnaby |
| 4,255,836 A | 3/1981 | Dunahoo |
| 4,257,309 A | 3/1981 | Dunahoo |
| 4,319,428 A | 3/1982 | Fox |
| 4,469,101 A | 9/1984 | Coleman et al. |
| 4,510,934 A | 4/1985 | Batra |
| 4,527,564 A | 7/1985 | Eguchi et al. |
| 4,582,165 A | 4/1986 | Latini |
| 4,604,821 A | 8/1986 | Moser |
| 4,705,040 A | 11/1987 | Mueller et al. |
| 4,723,634 A | 2/1988 | Fisk |
| 4,750,492 A | 6/1988 | Jacobs |
| 4,773,910 A | 9/1988 | Chen et al. |
| 4,781,191 A | 11/1988 | Thompson |
| 4,890,363 A | 1/1990 | Cross |
| 4,910,834 A | 3/1990 | Minkler |
| 4,946,377 A | 8/1990 | Kovach |
| 4,962,929 A | 10/1990 | Melton, Jr. |
| 4,971,075 A | 11/1990 | Lee |
| 5,062,344 A | 11/1991 | Gerker |
| 5,074,291 A | 12/1991 | Carter |
| 5,083,875 A | 1/1992 | Cedrone |
| 5,139,520 A | 8/1992 | Rosenberg |
| 5,168,605 A | 12/1992 | Bartlett |
| 5,178,629 A | 1/1993 | Kammerer |
| 5,219,359 A | 6/1993 | McQuilkin et al. |
| 5,269,783 A | 12/1993 | Sander |
| 5,306,290 A | 4/1994 | Martins et al. |
| 5,306,301 A | 4/1994 | Graf et al. |
| 5,374,268 A | 12/1994 | Sander |
| 5,374,269 A | 12/1994 | Rosenberg |
| 5,451,203 A | 9/1995 | Lamb |
| 5,505,735 A | 4/1996 | Li |
| 5,531,759 A | 7/1996 | Kensey et al. |
| 5,540,703 A | 7/1996 | Barker, Jr. et al. |
| 5,573,286 A | 11/1996 | Rogozinski |
| 5,575,819 A | 11/1996 | Amis |
| 5,628,756 A | 5/1997 | Barker |
| 5,649,541 A | 7/1997 | Stuckey |
| 5,667,528 A | 9/1997 | Colligan |
| 5,693,060 A | 12/1997 | Martin |
| 5,707,373 A | 1/1998 | Sevrain et al. |
| 5,769,894 A | 6/1998 | Ferragamo |
| 5,778,904 A | 7/1998 | Elsner |
| 5,921,986 A | 7/1999 | Bonutti |
| 5,928,267 A | 7/1999 | Bonutti et al. |
| 5,984,926 A | 11/1999 | Jones |
| 5,989,252 A | 11/1999 | Fumex |
| 6,030,007 A | 2/2000 | Bassily et al. |
| 6,045,551 A | 4/2000 | Bonutti |
| 6,056,752 A | 5/2000 | Roger |
| 6,117,160 A | 9/2000 | Bonutti |
| 6,143,029 A | 11/2000 | Rippstein |
| 6,203,572 B1 | 3/2001 | Johnson et al. |
| 6,238,395 B1 | 5/2001 | Bonutti |
| 6,258,091 B1 | 7/2001 | Sevrain et al. |
| 6,293,961 B2 | 9/2001 | Schwartz et al. |
| 6,296,659 B1 | 10/2001 | Foerster |
| 6,306,159 B1 | 10/2001 | Schwartz |
| 6,319,271 B1 | 11/2001 | Schwartz et al. |
| 6,342,060 B1 | 1/2002 | Adams |
| 6,418,576 B1 | 7/2002 | Starkweather |
| 6,453,974 B1 | 9/2002 | Lai et al. |
| 6,503,267 B2 | 1/2003 | Bonutti et al. |
| 6,517,578 B2 | 2/2003 | Hein |
| 6,527,795 B1 | 3/2003 | Lizardi |
| 6,533,802 B2 | 3/2003 | Bojarski et al. |
| 6,558,389 B2 | 5/2003 | Clark et al. |
| 6,589,244 B1 | 7/2003 | Sevrain et al. |
| 6,592,609 B1 | 7/2003 | Bonutti |
| 6,599,319 B2 | 7/2003 | Knudsen et al. |
| 6,602,290 B2 | 8/2003 | Esnouf et al. |
| 6,638,279 B2 | 10/2003 | Bonutti |
| 6,972,027 B2 | 12/2005 | Fallin et al. |
| 6,997,480 B2 | 2/2006 | Legrand |
| 6,997,940 B2 | 2/2006 | Bonutti |
| 7,033,380 B2 | 4/2006 | Schwartz et al. |
| 7,076,845 B2 | 7/2006 | Tylaska et al. |
| 7,150,757 B2 | 12/2006 | Fallin et al. |
| 7,235,091 B2 | 6/2007 | Thornes |
| 7,285,124 B2 | 10/2007 | Foerster |
| 7,306,417 B2 | 12/2007 | Dorstewitz |
| 7,390,332 B2 | 6/2008 | Selvitelli et al. |
| 7,407,512 B2 | 8/2008 | Bojarski et al. |
| 7,442,210 B2 | 10/2008 | Segal et al. |
| 7,481,825 B2 | 1/2009 | Bonutti |
| 7,500,990 B2 | 3/2009 | Whelan |
| 7,566,339 B2 | 7/2009 | Fallin et al. |
| 7,594,923 B2 | 9/2009 | Fallin et al. |
| 7,601,165 B2 | 10/2009 | Stone |
| 7,641,694 B1 | 1/2010 | Goble et al. |
| 7,658,751 B2 | 2/2010 | Stone et al. |
| 7,682,374 B2 | 3/2010 | Foerster et al. |
| 7,686,838 B2 | 3/2010 | Wolf et al. |
| 7,703,372 B1 | 4/2010 | Shakespeare |
| 7,722,644 B2 | 5/2010 | Fallin et al. |
| 7,749,250 B2 | 7/2010 | Stone et al. |
| 7,776,039 B2 | 8/2010 | Bernstein et al. |
| 7,806,909 B2 | 10/2010 | Fallin et al. |
| 7,845,669 B2 | 12/2010 | Yeh et al. |
| 7,846,181 B2 | 12/2010 | Schwartz et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,887,551 B2 | 2/2011 | Bojarski et al. |
| 7,892,238 B2 | 2/2011 | DiPoto et al. |
| 7,892,256 B2 | 2/2011 | Grafton et al. |
| 7,901,431 B2 | 3/2011 | Shumas |
| 7,905,903 B2 | 3/2011 | Stone et al. |
| 7,959,650 B2 | 6/2011 | Kaiser |
| 8,012,171 B2 | 9/2011 | Schmieding |
| 8,088,130 B2 | 1/2012 | Kaiser et al. |
| 8,118,836 B2 | 2/2012 | Denham et al. |
| 8,127,652 B1 | 3/2012 | Hennings et al. |
| 8,128,658 B2 | 3/2012 | Kaiser et al. |
| 8,136,438 B2 | 3/2012 | Shakespeare |
| 8,137,382 B2 | 3/2012 | Denham et al. |
| 8,147,514 B2 | 4/2012 | Bonutti |
| 8,202,298 B2 | 6/2012 | Cook et al. |
| 8,221,455 B2 | 7/2012 | Shumas et al. |
| 8,231,654 B2 | 7/2012 | Kaiser et al. |
| 8,257,394 B2 | 9/2012 | Saadat et al. |
| 8,298,271 B2 | 10/2012 | Jacene et al. |
| 8,366,744 B2 | 2/2013 | Bojarski et al. |
| 8,388,655 B2 | 3/2013 | Fallin et al. |
| 8,398,678 B2 | 3/2013 | Baker et al. |
| 8,439,976 B2 | 5/2013 | Albertorio et al. |

(56) References Cited

U.S. PATENT DOCUMENTS

| | | |
|---|---|---|
| 8,460,379 B2 | 6/2013 | Albertorio et al. |
| 8,475,534 B2 | 7/2013 | Kames et al. |
| 8,512,376 B2 | 8/2013 | Thornes |
| 8,523,943 B2 | 9/2013 | Hart |
| 8,535,313 B1 | 9/2013 | Masson |
| 8,591,578 B2 | 11/2013 | Albertorio et al. |
| 8,617,185 B2 | 12/2013 | Bonutti et al. |
| 8,628,573 B2 | 1/2014 | Roller et al. |
| 8,753,375 B2 | 6/2014 | Albertorio |
| 8,790,370 B2 | 7/2014 | Spenciner et al. |
| 8,808,329 B2 | 8/2014 | Bonutti |
| 8,876,900 B2 | 11/2014 | Guederian et al. |
| 8,882,816 B2 | 11/2014 | Kartalian et al. |
| 8,888,815 B2 | 11/2014 | Holmes, Jr. |
| 8,926,662 B2 | 1/2015 | Perriello et al. |
| 8,961,575 B2 | 2/2015 | Choinski |
| 8,998,904 B2 | 4/2015 | Zeetser et al. |
| 9,005,245 B2 | 4/2015 | Thornes et al. |
| 9,072,510 B2 | 7/2015 | Thornes et al. |
| 9,757,113 B2 | 9/2017 | Pasquali et al. |
| 2002/0029066 A1 | 3/2002 | Foerster |
| 2004/0153153 A1 | 8/2004 | Elson et al. |
| 2004/0254593 A1 | 12/2004 | Fallin et al. |
| 2006/0064126 A1 | 3/2006 | Fallin et al. |
| 2006/0089646 A1 | 4/2006 | Bonutti |
| 2006/0190042 A1 | 8/2006 | Stone et al. |
| 2006/0293710 A1* | 12/2006 | Foerster ............ A61B 17/0401 606/232 |
| 2008/0027446 A1 | 1/2008 | Stone et al. |
| 2008/0046009 A1 | 2/2008 | Albertorio et al. |
| 2008/0287991 A1 | 11/2008 | Fromm |
| 2009/0082805 A1 | 3/2009 | Kaiser et al. |
| 2009/0234377 A1 | 9/2009 | Mahlin et al. |
| 2009/0281568 A1 | 11/2009 | Cendan et al. |
| 2009/0312776 A1 | 12/2009 | Kaiser et al. |
| 2009/0312792 A1 | 12/2009 | Fallin et al. |
| 2010/0069926 A1 | 3/2010 | Goble et al. |
| 2010/0106194 A1 | 4/2010 | Bonutti et al. |
| 2010/0249809 A1 | 9/2010 | Singhatat et al. |
| 2010/0256677 A1 | 10/2010 | Albertorio et al. |
| 2010/0268273 A1 | 10/2010 | Albertorio et al. |
| 2010/0292733 A1 | 11/2010 | Hendricksen et al. |
| 2010/0305585 A1 | 12/2010 | Fallin et al. |
| 2010/0318126 A1 | 12/2010 | Fallin et al. |
| 2011/0022061 A1 | 1/2011 | Orphanos et al. |
| 2011/0022083 A1 | 1/2011 | DiMatteo et al. |
| 2011/0060375 A1 | 3/2011 | Bonutti |
| 2011/0077667 A1 | 3/2011 | Singhatat et al. |
| 2011/0098727 A1 | 4/2011 | Kaiser et al. |
| 2011/0144699 A1 | 6/2011 | Fallin et al. |
| 2011/0152927 A1 | 6/2011 | Deng et al. |
| 2011/0160749 A1 | 6/2011 | Gordon et al. |
| 2011/0160856 A1 | 6/2011 | Sinnott et al. |
| 2011/0190815 A1 | 8/2011 | Saliman |
| 2011/0208240 A1 | 8/2011 | Stone et al. |
| 2011/0218625 A1 | 9/2011 | Berelsman et al. |
| 2011/0238111 A1 | 9/2011 | Frank |
| 2011/0276137 A1 | 11/2011 | Seedhom et al. |
| 2011/0301708 A1 | 12/2011 | Stone et al. |
| 2012/0046693 A1 | 2/2012 | Denham et al. |
| 2012/0046747 A1 | 2/2012 | Justin et al. |
| 2012/0053630 A1 | 3/2012 | Denham et al. |
| 2012/0059416 A1 | 3/2012 | Justin et al. |
| 2012/0059468 A1 | 3/2012 | Mattern et al. |
| 2012/0065731 A1 | 3/2012 | Justin et al. |
| 2012/0065732 A1 | 3/2012 | Roller et al. |
| 2012/0109129 A1 | 5/2012 | Bernstein |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0123541 A1 | 5/2012 | Albertorio et al. |
| 2012/0150203 A1 | 6/2012 | Brady et al. |
| 2012/0150297 A1 | 6/2012 | Denham et al. |
| 2012/0158051 A1 | 6/2012 | Foerster |
| 2012/0158053 A1 | 6/2012 | Paulos |
| 2012/0165867 A1 | 6/2012 | Denham et al. |
| 2012/0165938 A1 | 6/2012 | Denham et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296375 A1 | 11/2012 | Thal |
| 2012/0303059 A1 | 11/2012 | Saadat et al. |
| 2012/0310279 A1 | 12/2012 | Sikora et al. |
| 2013/0023942 A1 | 1/2013 | Wyman et al. |
| 2013/0035722 A1 | 2/2013 | McDevitt et al. |
| 2013/0053901 A1 | 2/2013 | Cormier et al. |
| 2013/0066371 A1 | 3/2013 | Rogers et al. |
| 2013/0096612 A1 | 4/2013 | Zajac et al. |
| 2013/0123810 A1 | 5/2013 | Brown et al. |
| 2013/0123841 A1 | 5/2013 | Lyon |
| 2013/0138150 A1 | 5/2013 | Baker et al. |
| 2013/0165972 A1 | 6/2013 | Sullivan |
| 2013/0165973 A1 | 6/2013 | Fallin et al. |
| 2013/0172944 A1 | 7/2013 | Fritzinger et al. |
| 2013/0197576 A1 | 8/2013 | Catania et al. |
| 2013/0197577 A1 | 8/2013 | Wolf et al. |
| 2013/0197578 A1 | 8/2013 | Gregoire et al. |
| 2013/0197579 A1 | 8/2013 | Foerster et al. |
| 2013/0197580 A1* | 8/2013 | Perriello ............ A61F 2/0811 606/232 |
| 2013/0268000 A1 | 10/2013 | Harner et al. |
| 2013/0268073 A1 | 10/2013 | Albertorio et al. |
| 2013/0317544 A1 | 11/2013 | Ferguson et al. |
| 2014/0074239 A1 | 3/2014 | Albertorio et al. |
| 2014/0081399 A1 | 3/2014 | Roller et al. |
| 2014/0142627 A1 | 5/2014 | Hendricksen et al. |
| 2014/0257346 A1 | 9/2014 | Sengun et al. |
| 2014/0330312 A1 | 11/2014 | Spenciner et al. |
| 2015/0039026 A1 | 2/2015 | Pasquali et al. |
| 2015/0073477 A1 | 3/2015 | Holmes, Jr. |

FOREIGN PATENT DOCUMENTS

| | | |
|---|---|---|
| FR | 2743294 A1 | 7/1997 |
| JP | 2004-528121 A | 9/2004 |
| JP | 2009-521289 A | 6/2009 |
| WO | 92/006648 A1 | 4/1992 |
| WO | 02/91959 A1 | 11/2002 |
| WO | 2006/108114 A2 | 10/2006 |
| WO | 2007/073563 A2 | 6/2007 |
| WO | 2010/077591 A2 | 7/2010 |
| WO | 2013/116573 A1 | 8/2013 |

OTHER PUBLICATIONS

Chinese Office Action for Application No. 201410373458.1, dated May 15, 2017 (17 pages).

Japanese Office Action for Application No. 2014-154664, dated Apr. 17, 2018 (12 pages).

* cited by examiner

ADJUSTABLE GRAFT FIXATION DEVICE

CROSS-REFERENCE TO RELATED APPLICATION

This application is a divisional of U.S. patent application Ser. No. 14/340,683, entitled "ADJUSTABLE GRAFT FIXATION DEVICE," and filed on Jul. 25, 2014, which claims priority to U.S. Provisional Application No. 61/860,680, entitled "ADJUSTABLE GRAFT FIXATION DEVICE," and filed on Jul. 31, 2013, each of which is incorporated by reference herein in its entirety.

FIELD

The application relates generally to surgical procedures and, more particularly, to methods and devices for securing a soft tissue graft to bone.

BACKGROUND

Ligaments are the fibrous tissue that connects bones to other bones within the body. When ligaments are damaged, surgical reconstruction can be necessary, as the ligaments may not regenerate on their own. A number of surgical procedures exist for re-attaching ligaments, or other soft tissue, to bone. One example is the knee 100 shown in FIG. 1, which includes anterior and posterior cruciate ligaments 102, 104 extending from the head of the tibia 106 to the intercondylar notch of the femur 108. These ligaments operate to prevent forward and backward relative motion between the two bones. When ruptured (e.g., as can happen in strenuous athletic movements), surgical reconstruction can be necessary.

Tears in the cruciate ligaments of the knee can be repaired using a ligament graft taken from a cadaver (i.e., an allograft) or from a patient's own tissue (i.e., an autograft). Reconstruction procedures generally involve forming a hole in both the femur and tibia, and then securing opposite ends of the ligament graft in these holes. In one cruciate ligament repair procedure, a ligament graft is associated with a surgical implant and secured to the femur. A common femoral fixation means includes an elongate "button," sometimes referred to as a cortical button. The cortical button is attached to a suture loop that is sized to allow an adequate length of the soft tissue graft to lie within the femoral tunnel while providing secure extra-cortical fixation.

Existing devices and methods can be limited because they do not always provide the desired strength or adjustability. In some instances for example, one or more knots tied to help maintain a location of the suture loop with respect to a cortical button, and thus the graft associated therewith, can loosen or slip. Thus, even if a ligament graft is disposed at a desired location during a procedure, post-operatively the circumference of the loop can increase, causing the graft to move away from the desired location. Further, it can be desirable to limit the number of knots used in conjunction with such devices, because of the potential for the knots loosening and because the additional surface area of the knots can increase the risk of trauma to surrounding tissue. Still further, existing devices and methods also lack adjustability in many instances. For example, in procedures in which multiple ligament grafts are associated with the cortical button, it can be difficult to control placement of one ligament graft without also moving the other ligament graft.

Accordingly, there is a need for improved graft fixation devices and methods for use in repair and reconstruction procedures that include, for example, the cruciate ligaments of the knee. In particular, there is a need for devices and methods for positioning and securing ligament grafts that provide increased strength and adjustability while minimizing the number of knots used.

SUMMARY

The methods and devices described herein address these and other problems and provide for improved fixation of soft tissue grafts or other tissue to bone. The methods and devices described herein can provide a number of advantages over the art, including greater flexibility for positioning a graft being secured, as well as increased strength once the graft is secured. Further, the methods and devices described herein minimize the number of knots utilized in securing tissue to bone.

The methods and devices described herein generally provide a body having one or more through-holes formed therein and an associated suture length threaded through the body in a manner that provides a plurality of suture loops and a locking knot. The size of each of the suture loops can be adjusted simultaneously or selectively using the terminal ends of the suture length. In use, a graft placed through one or more of the suture loops extending from the body can be securely positioned within a bone tunnel by placing the body outside of the tunnel and securing the locking knot, as described in more detail herein.

In one aspect, a surgical implant can include an elongate body having a longitudinal axis extending therealong and having first and second through-holes that are offset to a first side of the longitudinal axis and a third through-hole that is offset to a second side of the longitudinal axis and that is positioned between the first and second through-holes. The surgical implant can also include a suture length extending through the first, second, and third through-holes such that a self-locking knot is formed on a first side of the body and a plurality of suture loops are formed on a second side of the body opposite the first side.

The devices and methods described herein can include any number of variations or additional features, all of which are considered within the scope of the present invention. For example, in some embodiments, the self-locking knot can be positioned over at least one of the first and second through-holes. The through-holes themselves can include a number of variations as well. For example, in some embodiments, a diameter of each of the first and second through-holes can be greater than a diameter of the third through-hole. The diameter of each of the first and second through-holes can be about 1.6 mm in certain embodiments.

In other embodiments, the self-locking knot can be formed by first and second terminal ends of the suture length extending through the third through-hole and passing through a loop formed from a mid-portion of the suture length that extends from the first through-hole. The first and second terminal ends can be separate from one another in some embodiments, while in others the first and second terminal ends can be spliced together. Splicing together the first and second terminal ends can reduce the number of suture lengths that must be managed and/or manipulated by a user, thereby reducing complexity and the potential for confusion during use.

In still other embodiments, the surgical implant can further include a fourth through-hole and a fifth through-hole centered on the longitudinal axis, where the first and second through-holes are positioned between the fourth and fifth through-holes. Moreover, in some embodiments the second side of the body can includes cut-outs that extend along the longitudinal axis and are in communication with the fourth and fifth through-holes.

The implant can have any of a variety of sizes. For example, in some embodiments a length of the body extending along the longitudinal axis can be in a range of about 5 mm to about 20 mm, a width of the body extending along the first side or the second side of the body can be in a range of about 2 mm to about 6 mm, and a thickness of the body extending between the first side and the second side of the body can be in a range of about 1 mm to about 3 mm. In certain embodiments, the length of the body extending along the longitudinal axis can be about 12 mm, the width of the body extending along the first side or the second side of the body can be about 4.25 mm, and a thickness of the body extending between the first side and the second side of the body can be about 2 mm.

The body of the surgical implant can be formed from a variety of materials suitable for implantation in a patient's body. In some embodiments, for example, the body can be formed from titanium. In other embodiments, however, other suitably rigid and biocompatible materials can be employed, including, for example, stainless steel and biocompatible polymers such as polyether ether ketone (PEEK), bioabsorbable elastomers, copolymers such as polylactic acid-polyglycolic acid (PLA-PGA), and bioabsorbable polymers such as polylactic acid.

In another aspect, a surgical implant, can include an elongate body having a longitudinal axis extending therealong and having first and second through-holes that are centered on the longitudinal axis and a third through-hole that is offset from the longitudinal axis and that is positioned between the first and second through-holes. The surgical implant can further include a suture length extending through the first, second, and third through-holes such that a self-locking knot is formed on a first side of the body and a plurality of suture loops are formed on a second side of the body opposite the first side.

Methods for preparing and securing a surgical implant are also provided. In one aspect, a method for preparing a surgical implant can include threading first and second terminal ends of a suture length through a first through-hole formed in a body such that a securing loop formed from a mid-portion of the suture length extends above the first through-hole on a first side of the body. The method can further include threading the first and second terminal ends of the suture length through a second through-hole formed in the body to create first and second fixation loops extending below a second side of the body opposite the first side. The method can also include threading the first and second terminal ends of the suture length through the first through-hole such that they extend below the second side of the body. The method can further include threading the first and second terminal ends of the suture length through a third through-hole formed in the body to create third and fourth fixation loops extending below the second side of the body, wherein the third through-hole is positioned between the first through-hole and the second through-hole and an axis of a center of the third through-hole is offset from an axis extending through centers of the first and second through-holes, as well as threading the first and second terminal ends of the suture length through the securing loop formed on the first side of the body.

A number of variations and additional steps are possible in the methods described herein. For example, in some embodiments the method can further include applying tension to the first and second terminal ends of the suture length to collapse the securing loop and form a self-locking knot positioned over the first through-hole. In certain embodiments the method can further include forming at least one half hitch using the first and second terminal ends of the suture length to further secure the self-locking knot.

In other embodiments, the method can further include extending a soft tissue graft through at least one of the fixation loops extending from the second side of the body. In addition, in certain embodiments the soft tissue graft can be extended through the first and second fixation loops, and the method can further include extending a second soft tissue graft through the third and fourth fixation loops.

In certain embodiments, the method can further include extending a soft tissue graft through each of the fixation loops extending from the second side of the body. Still further, in some embodiments the method can further include twisting the third and fourth fixation loops 180° prior to extending the soft tissue graft therethrough.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. Further, the features illustrated or described in connection with one exemplary embodiment may be combined with the features of other embodiments. Such modifications and variations are intended to be included within the scope of the present invention.

The present invention is generally directed to methods and devices for securing a soft tissue graft to bone. Surgical implants described herein generally include a body, otherwise known as a "cortical button," and an associated suture length threaded through the body in a manner that provides a plurality of suture loops and a self-locking knot. The size of each of the suture loops can be adjusted simultaneously or selectively using the terminal ends of the suture length. In use, a graft placed through one or more of the suture loops extending from the body can be securely positioned within a bone tunnel by placing the body outside of the tunnel and securing the self-locking knot.

An example of a surgical implant for securing a tissue graft to bone is described in U.S. patent application Ser. No. 13/793,514, filed Mar. 11, 2013, and entitled "Implant Having Adjustable Filament Coils." The entire content of this application is hereby incorporated by reference.

Figure 1:
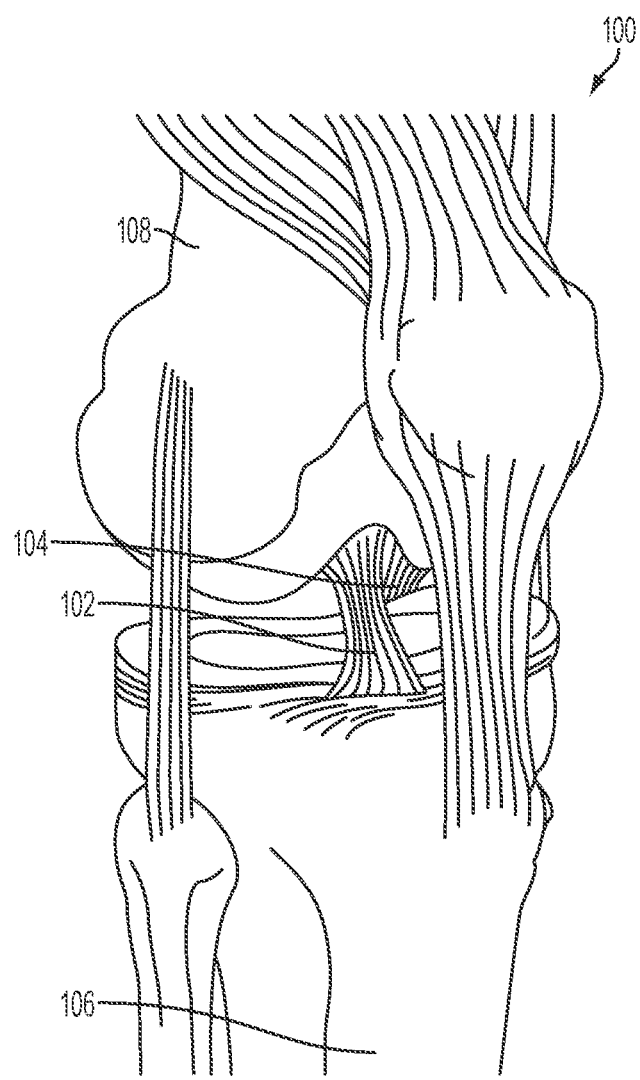
FIG. 1 is an illustration of the anatomy of a human knee.
Figure 2:
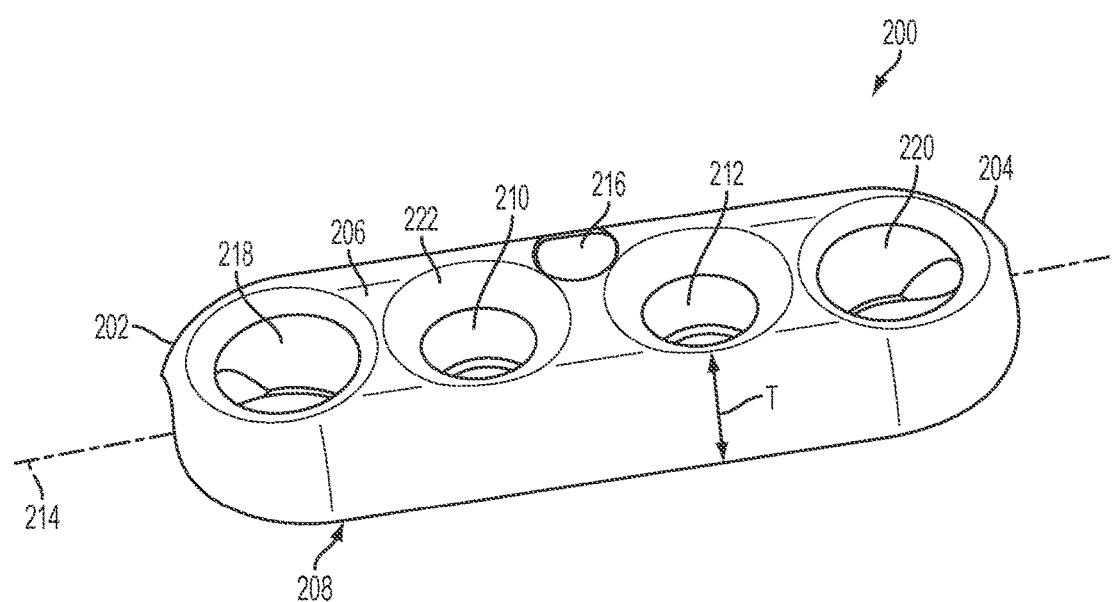
FIG. 2 is a perspective view of one embodiment of a fixation body.
Figure 3:
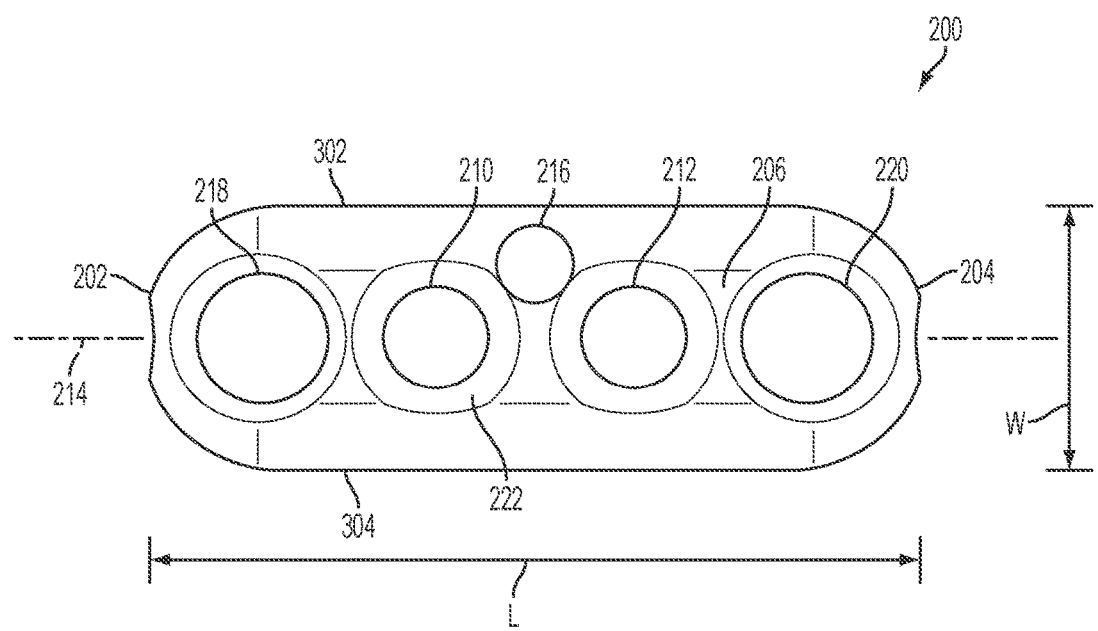
FIG. 3 is a top view of the fixation body of FIG. 2.
Figure 4:
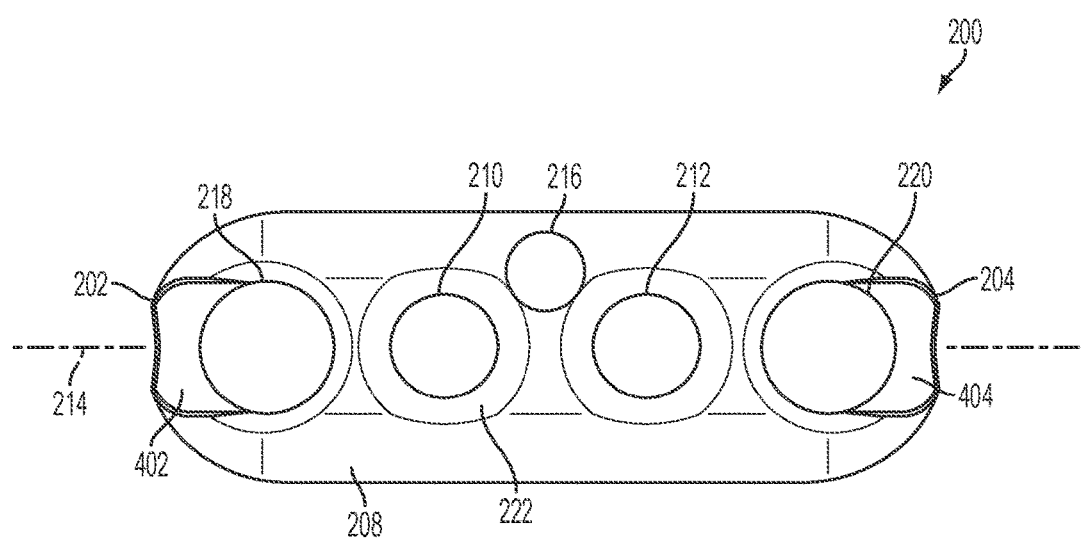
FIG. 4 is a bottom view of the fixation body of FIG. 2.

FIGS. 2-4 illustrate one embodiment of a body 200 according to the teachings of the present invention. The body (also known as a "cortical button") 200 can have an elongate, somewhat rectangular shape with rounded or curved terminal ends 202, 204. A plurality of through-holes can be formed in the body extending between a first side 206 and a second, opposing side 208. A first through-hole 210 and a second through-hole 212 can be adjacent to one another and positioned such that their centers lie along a longitudinal axis 214 of the body 200. A third through-hole 216 can be positioned between the first through-hole 210 and the second through-hole 212, and its center can be offset by a distance from the longitudinal axis 214, as shown in the figures. The body 200 can also include fourth and fifth through-holes 218, 220 positioned outside the first and second through-holes 210, 212 near the terminal ends 202, 204 of the body. These through-holes can also be centered along the longitudinal axis 214.

As shown, the first through fourth through-holes 210, 212, 218, 220 can have diameters that are substantially the same, and a space separating the adjacent through-holes can be substantially the same for each adjacent pair. As shown in FIG. 3, a length L of the body 200 can be defined by a distance between the terminal ends 202, 204 and a width W can be defined by a distance between first and second sidewalls 302, 304 of the body 200 extending along the first or second surfaces 206, 208. The body 200 can also have a thickness T defined by a distance between the first and second surfaces 206, 208, as shown in FIG. 2.

In some embodiments, the length L of the body 200 can be in a range of about 5 mm to about 20 mm, the width W can be in a range of about 2 mm to about 6 mm, and the thickness T can be in a range of about 1 mm to about 3 mm. In one exemplary embodiment, the length L can be about 12 mm, the width W can be about 4.25 mm, and the thickness T can be about 2 mm.

Diameters of the through-holes 210, 212, 216, 218, 220 can be in a range of about 1 mm to about 2 mm. The diameters of the first and second through-holes 210, 212 can be selected such that a self-locking knot formed from a suture length is unable to pass through the hole, as described in more detail below. Further, in some embodiments the third through-hole 216 can be smaller than the first and second through-holes 210, 212. For example, in one embodiment the diameters of the first, second, fourth, and fifth through-holes 210, 212, 218, 220 can be about 1.6 mm, and the diameter of the third through-hole 216 can be about 1.2 mm.

The body 200 can include one or more features that allow easier manipulation of suture lengths threaded therethrough. For example, a top edge 222 or a bottom edge 224 of any of the through holes 210, 212, 216, 218, 220 can be chamfered or rounded so as to ease threading of a suture length therethrough and reduce the possibility of damage to a suture length from contact with a sharp-edged corner. In addition, one or more cut-outs can be provided on the second surface 208 of the body 200 to facilitate pulling a suture length through one of the plurality of through-holes when the second surface 208 is, for example, pressed against the outer surface of a bone. As shown in the bottom view of FIG. 4, the illustrated body 200 includes a first cut-out 402 and a second cut-out 404 formed in the second surface 208. The cut-outs 402, 404 extend along the longitudinal axis 214 of the body and define a channel extending between the terminal ends 202, 204 and the fourth and fifth through-holes 218, 220. As a result, a suture length extending through the fourth or fifth through-holes 218, 220 can be passed through the cut-out 402 or 404 even if the second surface 208 is flush against another surface (e.g., a bone).

The body 200 illustrated in FIGS. 2-4 is merely one example of a body according to the teachings provided herein. A body configured to be associated with a suture length to create a surgical implant as described herein can have a variety of different shapes, sizes, and features, and can be made of a variety of different materials. These various shapes, sizes, and materials can depend, at least in part, on characteristics of other components with which the body is used, such as the suture length, the soft tissue graft type, etc. The shape, size, and material can also depend on the particular type of procedure being used to implant the body. Thus, while in the illustrated embodiment the body 200 is somewhat rectangular having curved terminal ends 202, 204, in other embodiments the body can be substantially tubular or have any of a variety of other shapes.

In addition, the placement of the plurality of through-holes formed through the body 200 can be varied as well. For example, in the illustrated embodiment the longitudinal axis 214 is shown as a central longitudinal axis of the body. However, in other embodiments the axis 214 may be offset toward one side of the body. The plurality of through-holes can similarly be offset, or can be angled with respect to the body 200. In addition, the first and second through-holes 210, 212 need not necessarily be centered along the same axis as the fourth and fifth through-holes 218, 220. The center of the third through-hole 216, however, should be offset from whatever axis is defined by the centers of the first and second through-holes 210, 212.

Figure 3A:
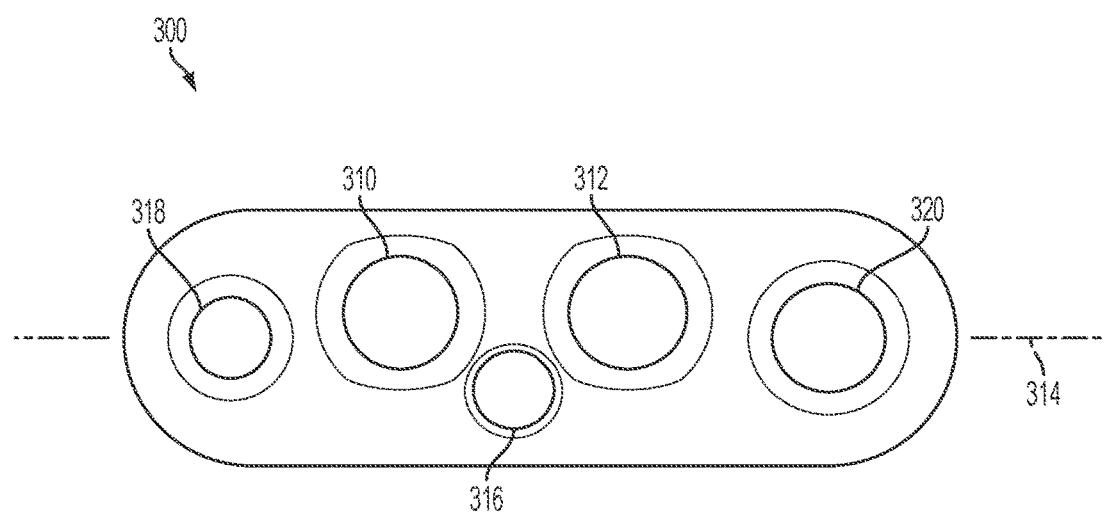
FIG. 3A is a top view of an alternative embodiment of a fixation body.

FIG. 3A illustrates one embodiment of a body 300 having an alternative arrangement of through-holes. In particular, the body 300 includes first and second through-holes 310, 312 that are offset from a longitudinal axis 314 of the body 300. The first and second through-holes 310, 312 are offset to a first side of the longitudinal axis 314, and the distance of the offset (i.e., the distance along the lateral width W between the longitudinal axis and a line passing through the centers of the first and second through-holes) can be varied according to the particular embodiment. The body 300 can further include a third through-hole 316 that is offset to a second side of the longitudinal axis (i.e., opposite to the offset of the first and second through-holes). In the illustrated embodiment, the body 300 also includes fourth and fifth through-holes 318, 320, similar to the through-holes 218, 220 described above.

The body 200 can be formed from a variety of materials but, in some embodiments, can be formed from a biocompatible metal such as stainless steel or titanium. The body can also be formed from any number of polymers or other biocompatible materials. Non-limiting examples of biocompatible polymers and other materials can include polyether ether ketone (PEEK), bioabsorbable elastomers, copolymers such as polylactic acid-polyglycolic acid (PLA-PGA), and bioabsorbable polymers such as polylactic acid. Though any of a variety of materials can be suitable for use in a given embodiment, in certain embodiments a subset of materials can be preferred. For example, for implants used in conjunction with repairing the cruciate ligaments of the knee (e.g., the anterior cruciate ligament, or ACL), forming the body 200 from titanium can be preferred because it is able to withstand the significant forces experienced in anchoring the ACL.

Steps for configuring a suture length 500 for use in conjunction with the body 200 to form a surgical implant for securing a soft tissue graft are illustrated in FIGS. 5-10. A variety of different types, sizes, and lengths of suture material can be used as the suture length 500. Non-limiting examples can include cannulated filament, braided filament, or mono filament suture materials. The type, size, and strength of the suture length 500 can depend, at least in part, on the other materials of the implant including, for example, the material of the body 200, the type of graft, the bone or other tissue through which the implant will be passed, and the type of procedure in which the implant is used. In one exemplary embodiment, the suture length 500 can be a #0 filament (about 26 gauge to about 27 gauge), such as Orthocord™ filament that is commercially available from DePuy Mitek, Inc. of Raynham, Mass., or Ethibond™ filament that is commercially available from Ethicon, Inc. of Somerville, N.J. The thickness of the suture length 500 should provide strength to secure the graft but also minimize the trauma caused to tissue through which it passes. In some embodiments, the suture length 500 can have a diameter in a range of about a #5 filament (about 20 gauge to about 21 gauge) to about a #3-0 filament (about 29 gauge to about 32 gauge). The suture length 500 can in some embodiments be formed from a material that is entirely, or at least partially, bioabsorbable. Orthocord™, for example, is approximately 55-65% PDS™ polydioxanone, which is bioabsorbable, and about 35-45% ultra high molecular weight polyethylene, while Ethibond™ is primarily high strength polyester. The amount and type of bioabsorbable material used in the suture length 500 can be determined based on user preference and the type of procedure.

The length of the suture 500 can also be varied depending on user preference or the particular geometry of the implantation site. In some embodiments, a suture length 500 having an overall length in a range of about 0.2 meters to about 5 meters can be used. In particular embodiments, such as ACL repair procedures, it can be desirable to form suture loops (as described below) that are approximately 60 mm long initially to allow the body 200 to be drawn through a bone tunnel in the femur while the loops extend outside the tunnel. As a result, in some embodiments, a suture length 500 having an overall length of about 1.5 meters can be used.

Figure 5:
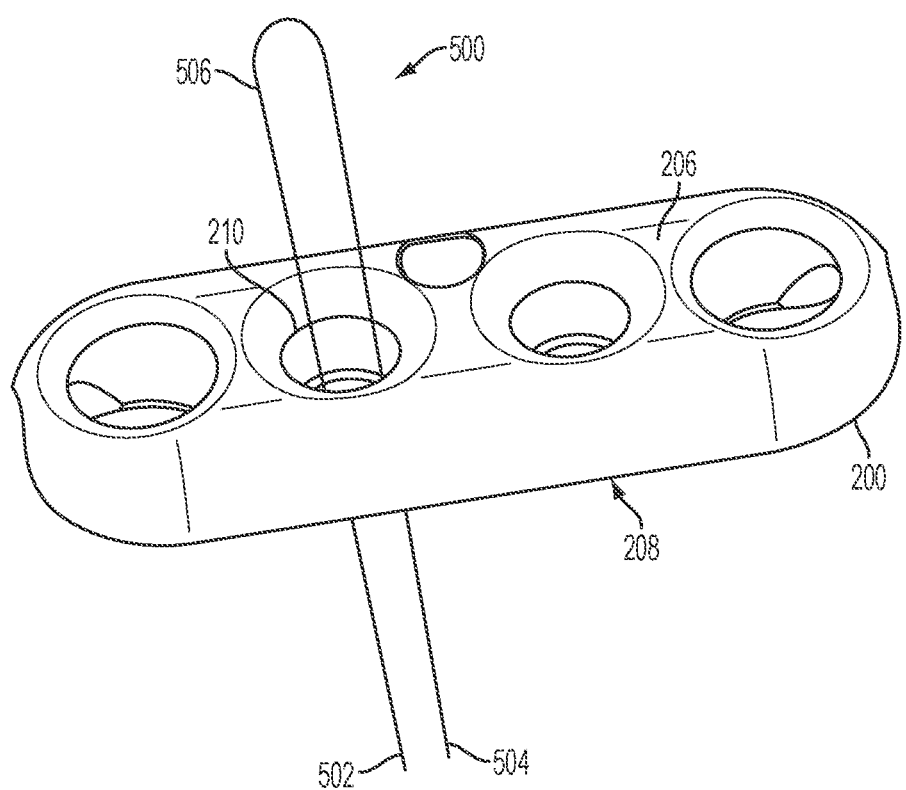
FIG. 5 is an illustration of one embodiment of a suture length passed through the fixation body of FIG. 2.

As shown in FIG. 5, the suture length 500 can be folded substantially in half and its first and second terminal ends 502, 504 can be threaded through the first through-hole 210 of the body 200 from the first side 206 to the second side 208 thereof. Threading the suture length 500 in this manner can create a securing loop 506 that extends above the first side 206 of the body 200 and is formed from a mid-portion of the suture length 500. This securing loop 506 can be used to form a self-locking knot on the first side 206 of the body 200, as described below.

Figure 6:
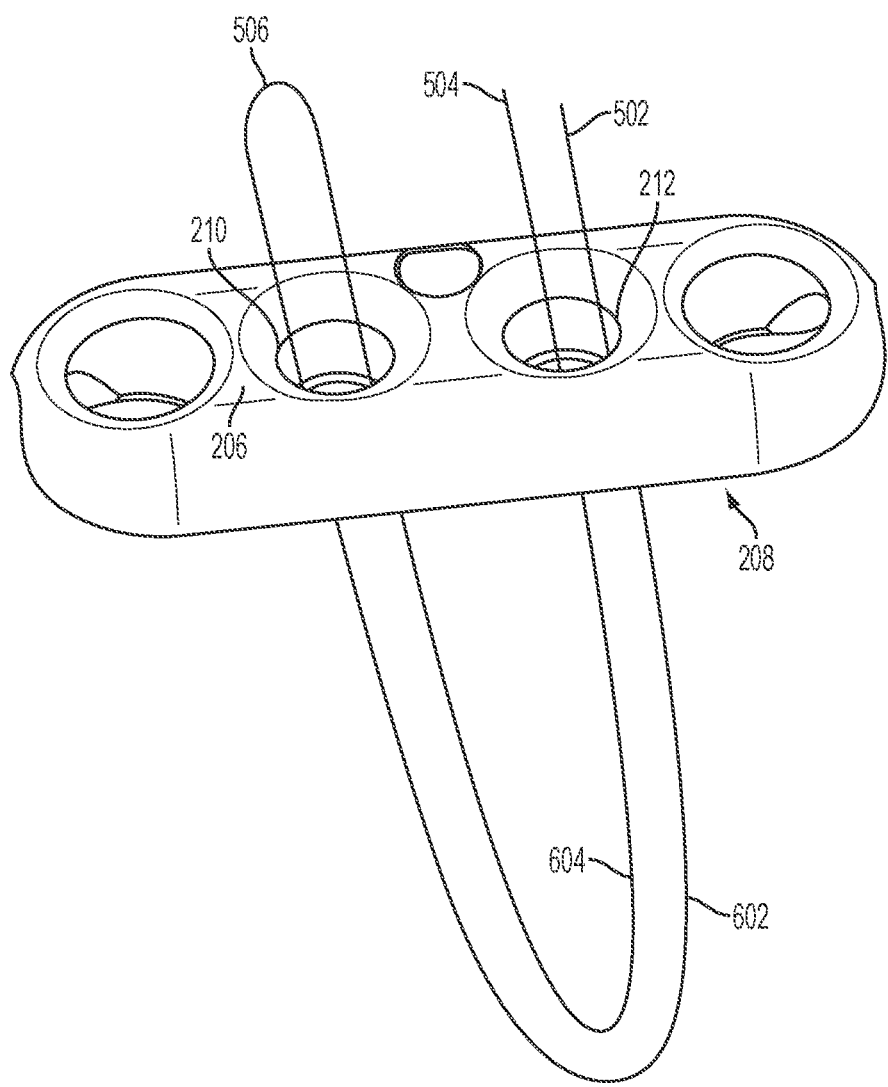
FIG. 6 is an illustration of the suture length of FIG. 5 passed through the fixation body of FIG. 2 a second time.

After the suture length 500 has been threaded through the first through-hole 210, the first and second terminal ends 502, 504 can be threaded through the second through-hole 212 from the second side 208 of the body 200 to the first side 206, as shown in FIG. 6. Threading the suture length 500 in this manner can create first and second fixation loops 602, 604 that extend below the second side 208 of the body 200.

Figure 7:
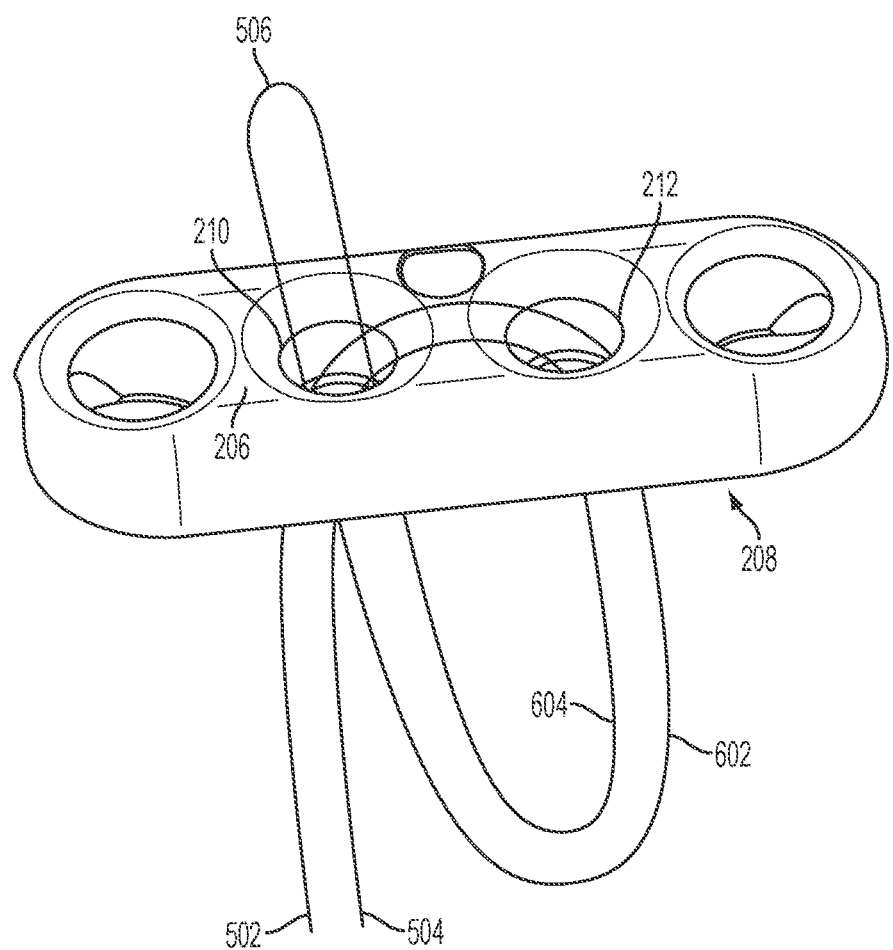
FIG. 7 is an illustration of the suture length of FIG. 5 passed through the fixation body of FIG. 2 a third time.
Figure 8:
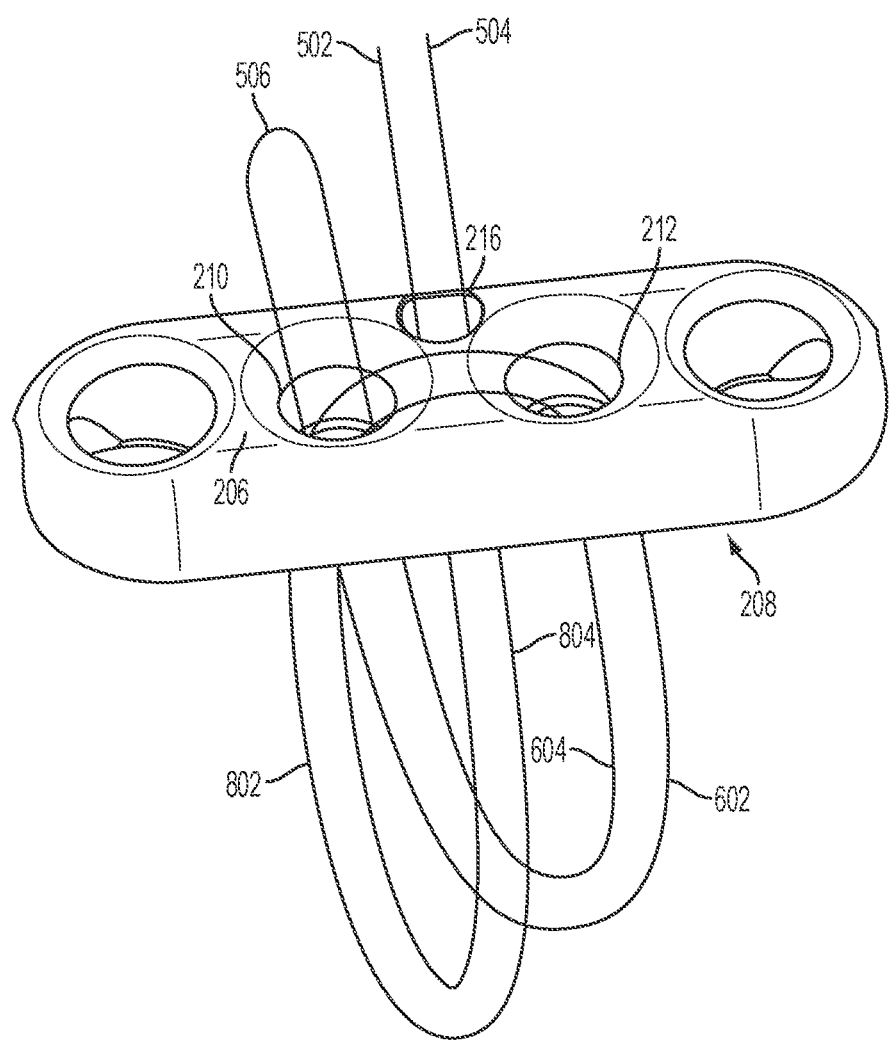
FIG. 8 is an illustration of the suture length of FIG. 5 passed though the fixation body of FIG. 2 a fourth time.

The first and second terminal ends 502, 504 can then be threaded through the first through-hole 210 a second time from the first side 206 to the second side 208 of the body 200, as shown in FIG. 7. The first and second terminal ends 502, 504 can then be threaded through the third through-hole 216 from the second side 208 of the body 200 to the first side 206. This can create third and fourth fixation loops 802, 804 that extend below the second side 208 of the body 200.

Figure 9:
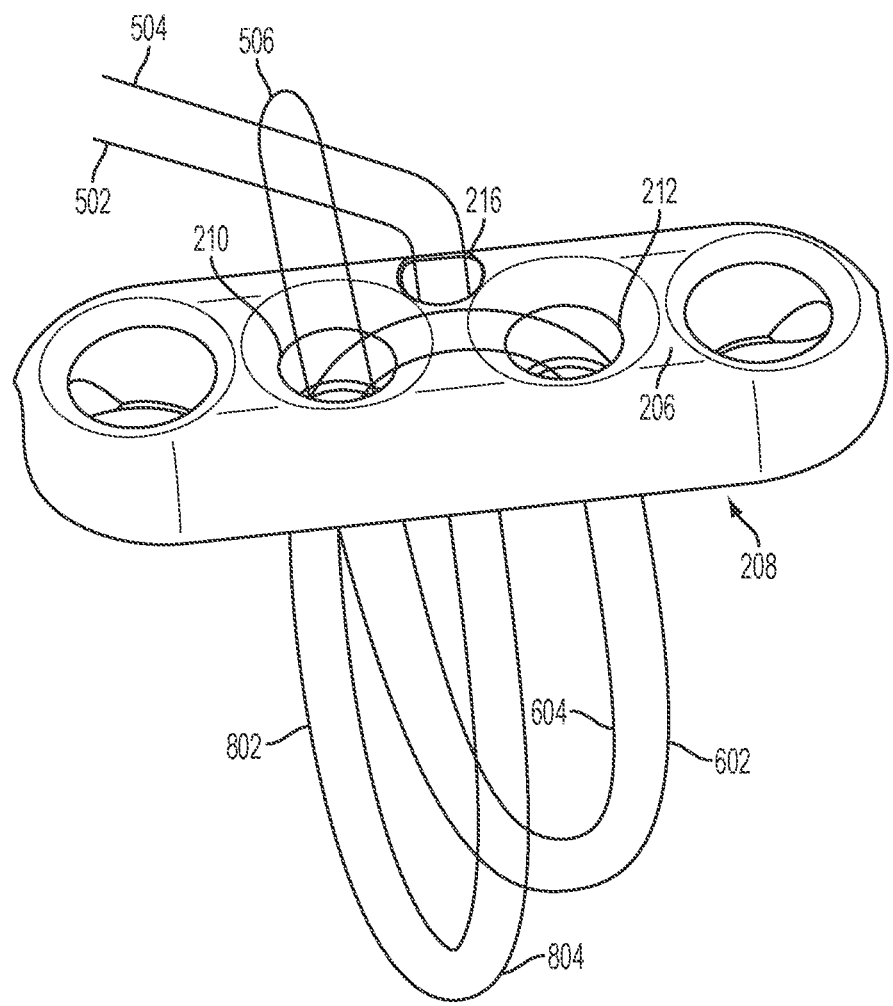
FIG. 9 is an illustration of one embodiment of a knot formed using the suture length of FIG. 5.
Figure 10:
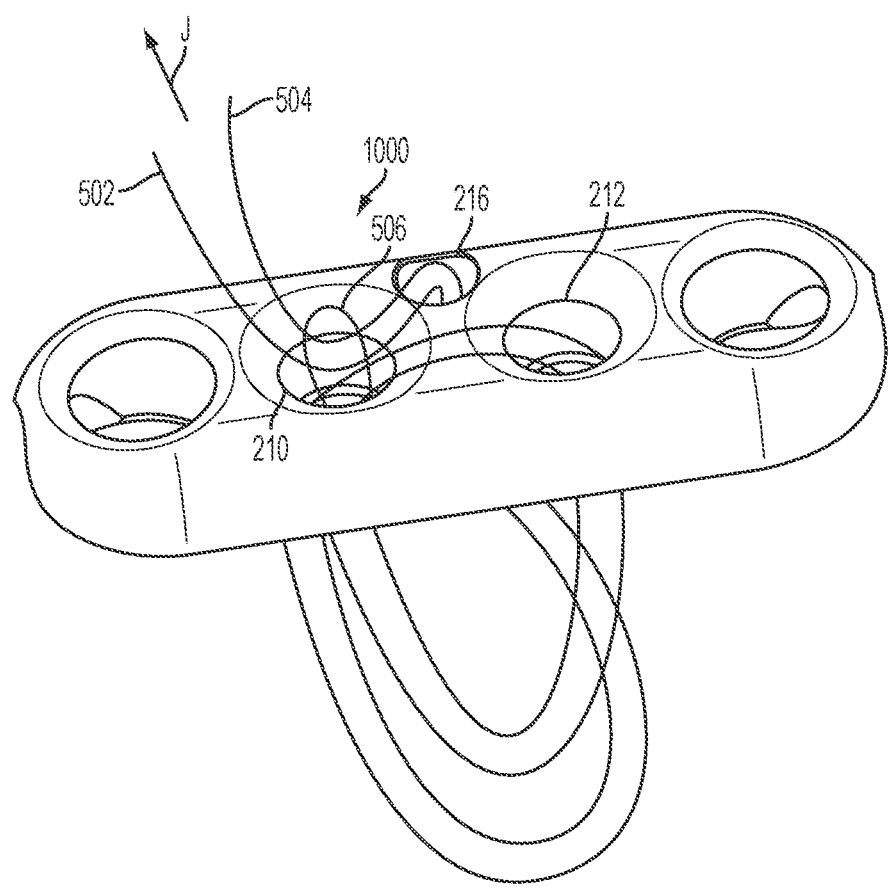
FIG. 10 is an illustration of the knot of FIG. 9 when tightened.

To secure the configuration of the implant, a self-locking knot can be formed on the first side 206 of the body 200. This can be done by threading the first and second terminal ends 502, 504 of the suture length 500 that extend from the third through-hole 216 through the securing loop 506 that extends from the first through-hole 210, as shown in FIG. 9. After threading the terminal ends 502, 504 of the suture length 500 through the securing loop 506, tension can be applied to the terminal ends (e.g., by pulling the ends in the direction of arrow J in FIG. 10) that can collapse the securing loop 506 and form a self-locking knot 1000 that is positioned over the first through-hole 210, as shown in FIG. 10. Tension can be applied to both terminal ends 502, 504 simultaneously, or can be applied in an alternating fashion to one terminal end at a time. In addition, counter-tension can be applied by pulling in an opposite direction on the fixation loops extending below the second side 208 of the body 200. This counter-tension can aid in securing the self-locking knot and drawing it into the first through-hole 210, as described below.

The self-locking knot 1000 can be secured by the friction between the securing loop 506 and the portions of the suture length 500 near the terminal ends 502, 504 that are in contact therewith. The self-locking ability of the knot 1000 is enhanced by the position of the knot 1000 over the first through-hole 210 (or the second through-hole 212, as either can be used). This is because the knot 1000 can be drawn into the first through-hole 210 by the collapse of the securing loop 506 as the first and second terminal ends 502, 504 of the suture length 500 are tensioned and as counter-tension is applied to the fixation loops extending from the opposite side of the body 200. Because the diameter of the first through-hole 210 is selected such that the knot 1000 cannot pass through the hole (as described above), the knot 1000 instead wedges into the first through-hole 210. The sidewalls of the first through-hole 210 therefore compress the knot and increase the friction between the various portions of the suture length 500.

The increased friction force provided to the knot 1000 by virtue of its positioning over the first through-hole 210 explains the need for the third through-hole 216 that is positioned between and offset from the first and second through-holes 210, 212. If, for example, the third through-hole 216 were not present and the suture length 500 were threaded only through the first and second through-holes 210, 212, it is possible that the entire grouping of suture loops could rotate or shift post-operatively such that the knot 1000 would come out of the first through-hole 210 and move toward the second through-hole 212. This could lead to loosening of the knot 1000 and the failure of the implant. By providing the third through-hole 216, movement of the grouping of suture loops and the knot 1000 can be restricted such that the knot 1000 remains over the first through-hole 210.

After the self-locking knot 1000 has been secured, the terminal ends 502, 504 of the suture length 500 can be left alone, or excess suture material can be trimmed off. In some embodiments, extra security for the self-locking knot 1000 can be provided by forming at least one half-hitch knot using either—or both—of the terminal ends 502, 504. Alternative forms of supplementary fixation can also be used. Non-limiting examples can include forming alternative supplementary knots known in the art using the terminal ends 502, 504, applying a crimp element to the terminal ends 502, 504, applying an adhesive to the knot 1000, or using any other suitable technique for ensuring that the knot 1000 does not loosen.

The size of the fixation loops 602, 604, 802, 804 extending below the second side 208 of the body 200 can be selectively adjusted independently or simultaneously. For example, the size of all four fixation loops 602, 604, 802, 804 can be adjusted by simultaneously pulling on the terminal ends 502, 504 of the suture length 500. Alternatively, for example, the size of the first and third fixation loops 602, 802 can be adjusted by pulling on the first terminal end 502 alone. The ability to selectively adjust the size of the various fixation loops can be desirable when using multiple tissue grafts in combination with a single implant. In such an embodiment, for example, a first tissue graft can be looped through the first and third fixation loops 602, 802 and a second tissue graft can be looped through the second and fourth fixation loops 604, 804. The first terminal end 502 of the suture length can then be tensioned to adjust the size of the first and third fixation loops 602, 802, and the second terminal end 504 can be tensioned to adjust the size of the second and fourth fixation loops 604, 804. In this manner, the end points of the first and second tissue grafts can be staggered at different distances from the second side 208 of the body 200, which can aid in positioning the multiple grafts in, for example, a single bone tunnel.

Figure 11:
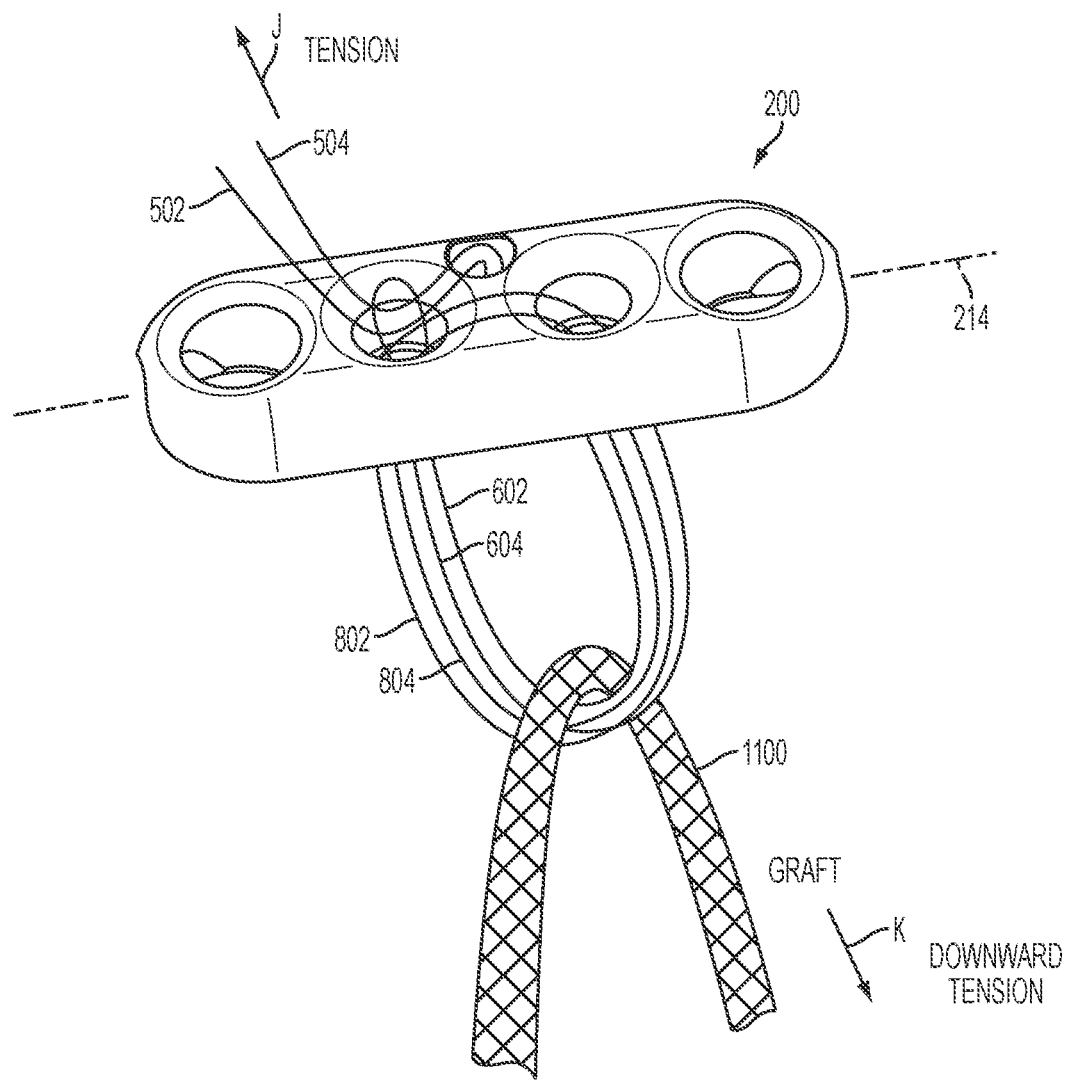
FIG. 11 is an illustration of one embodiment of an adjustable fixation implant.

As mentioned above, tensioning the first and second terminal ends 502, 504 of the suture length 500 can both secure the self-locking knot 1000 and reduce the size of the fixation loops 602, 604, 802, 804 extending below the second side 208 of the body 200. As a result, it can be desirable to provide counter-tension to aid in securing the knot and maintaining a desired size of the fixation loops. This can be done, for example, by tensioning a tissue graft, such as a ligament graft, in a direction opposite of the tension applied to the terminal ends 502, 504 of the suture length 500. The application of counter-tension is shown in FIG. 11, where tension is applied in the direction of arrow J to the terminal ends 502, 504 of the suture length 500 while an opposite tension in the direction of arrow K is applied to a ligament graft 1100 that is looped through all four fixation loops 602, 604, 802, 804.

As noted above, a ligament or other tissue graft 1100 can be coupled to one or more of the fixation loops 602, 604, 802, 804 in a variety of manners. In some embodiments, for example, a single graft can be looped through all four of the fixation loops. In other embodiments, multiple grafts can be looped through one or more fixation loops, e.g., two grafts can be looped through two separate pairs of fixation loops, etc. The presence of multiple fixation loops that can be selectively adjusted in size allows for a variety of different possible configurations.

Figure 12:
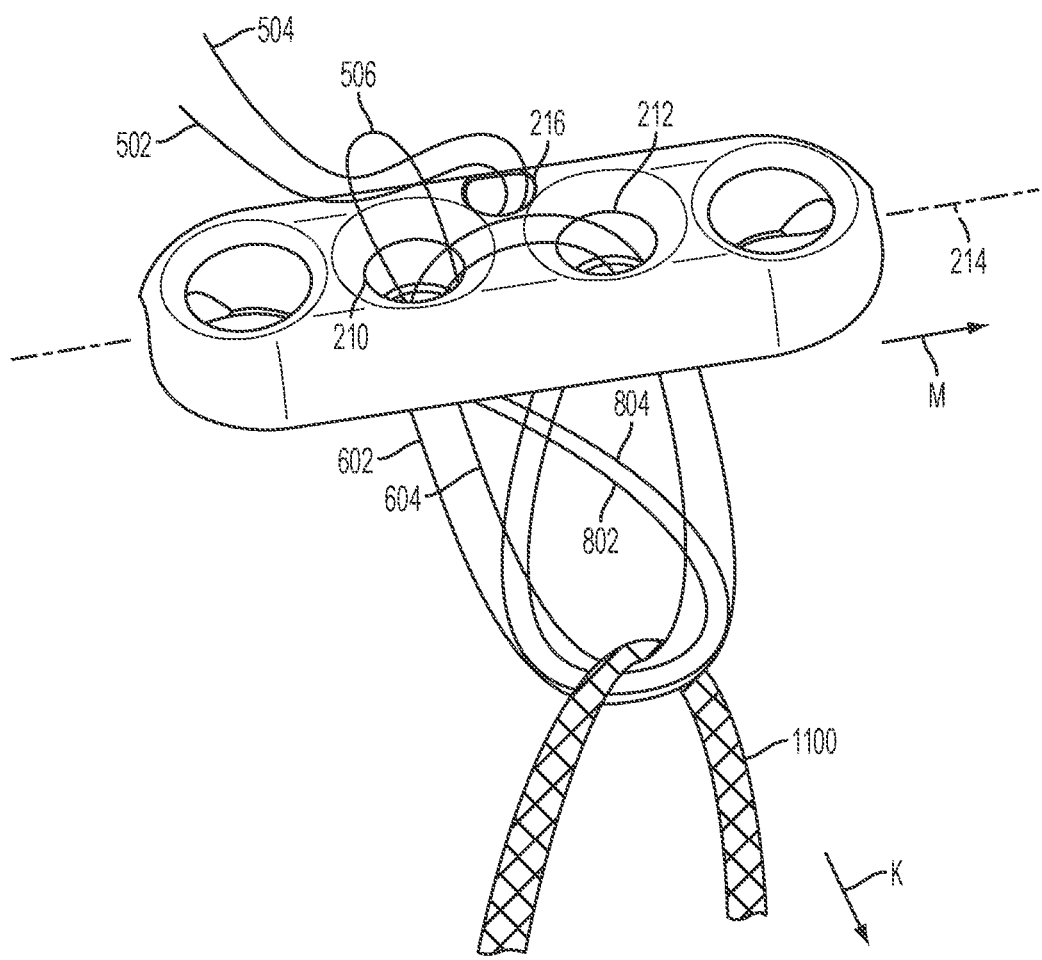
FIG. 12 is an illustration of an alternative embodiment of an adjustable fixation implant.

In addition, the fixation loops themselves can be manipulated in various ways to increase the ability of the implant to secure a graft. For example, FIG. 12 illustrates an alternative embodiment in which the third and fourth fixation loops 802, 804 are twisted or rotated by 180° before the graft 1100 is looped therethrough. Twisting the third and fourth fixation loops in this manner can help ensure that all four fixation loops 602, 604, 802, 804 evenly share the load of the ligament graft 1100 regardless of the direction of force experienced. For example, in the configuration shown in FIG. 11, the four fixation loops 602, 604, 802, 804 evenly share loads that are perpendicular to the longitudinal axis 214 of the body 200 (i.e., loads parallel to the arrow K). However, if a force is imparted along the line M shown in FIG. 12, i.e., a force that is parallel (or has a large enough component that is parallel) to the longitudinal axis 214, the knot 1000 can become loose as the terminal ends 502, 504 are drawn back through the securing loop 506 and into the third through-hole 216. Twisting the third and fourth fixation loops 802, 804, can provide increased resistance to loosening of the knot 1000 when these types of forces are applied.

As described above, surgical implants according to the teachings provided herein can be used in a variety of procedures to secure a soft tissue graft to bone. One common procedure is the repair of a torn or ruptured ACL in a patient's knee. An exemplary repair procedure can include forming a bone tunnel through a patient's tibia 106 and femur 108 in a manner known in the art. This can produce, for example, the bone tunnel 1300 illustrated in FIG. 13. An implant can be prepared by coupling a ligament graft taken from a cadaver or the patient's own tissue to a cortical button (e.g., body 200) and associated suture (e.g., suture length 500), as described above. In some embodiments, for example, an elongate graft 1100 can be looped through the four fixation loops 602, 604, 802, 804 such that a midportion of the graft is in contact with the fixation loops and opposing terminal ends of the graft are adjacent to one another (e.g., as shown in FIG. 11).

The body 200 can be introduced into the bone tunnel of the patient's tibia 106 and pulled through the tibia and femur 108 until the body 200 emerges on an outer portion of the patient's femur. In order to pull the body 200 through the bone tunnel, a shuttle suture (not shown) can be threaded through the fourth through-hole 218 that is near the first (front) terminal end 202 of the body 200. The shuttle suture can be used to pull the body through the bone tunnel 1300 along its longitudinal axis 214 so as to minimize the cross sectional area of the body. Pulling the body 200 in this manner can also pull the fixation loops 602, 604, 802, 804 and graft 1100 into the patient's body.

Figure 13:
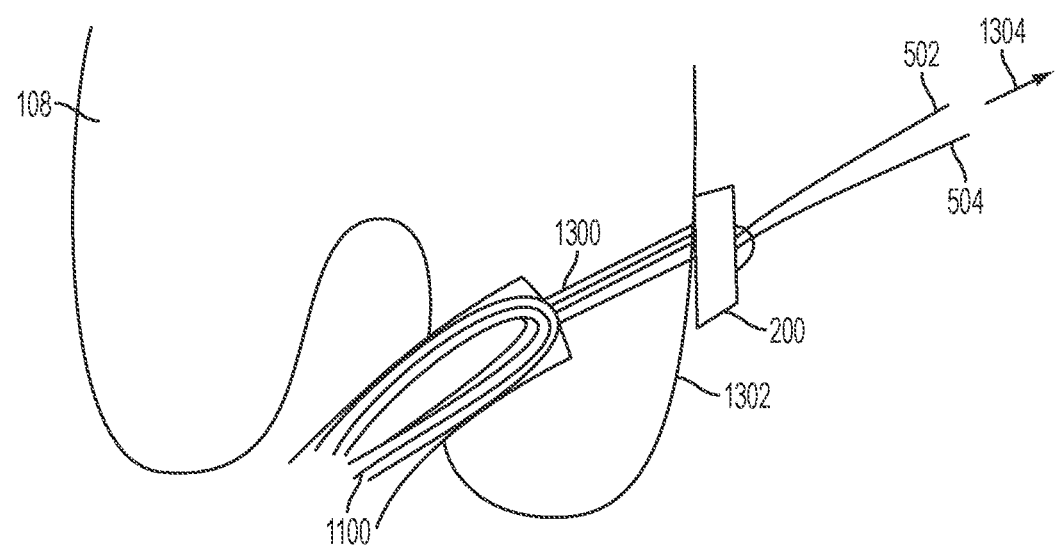
FIG. 13 is an illustration of one embodiment of an adjustable fixation implant in a femur.

After the body 200 emerges from the bone tunnel 1300 at an outer surface of the femur 1302, the body 200 can be flipped into an orientation that places the second side 208 flush against the outer surface of the femur such that the body 200 cannot reenter the bone tunnel 1300. Flipping the orientation of the body 200 can be accomplished by pulling on a rotation suture (not shown) that can be threaded through the fifth through-hole 220 near the second (rear) terminal end 204 of the body. It should be noted that both the shuttle and rotation sutures can be threaded through the fourth and fifth through-holes prior to introducing the body 200 into a bone tunnel. After the body 200 has been pulled through the bone tunnel and flipped so as to sit flush against an outer surface 1302 of the femur 108 (as shown in FIG. 13), the shuttle and rotation sutures can be removed by simply pulling on a free end thereof. The cut-outs 402, 404 that communicate with the fourth and fifth through-holes 218, 220 can facilitate the removal of the shuttle and rotation sutures despite the positioning of the body 200 flush against the outer surface 1302 of the femur 108.

The terminal ends 502, 504 can be tensioned in the direction of arrow 1304 to reduce the size of the fixation loops 602, 604, 802, 804 and draw the ligament graft 1100 into the bone tunnel 1300 formed in the femur 108, as shown in FIG. 13. The size of the fixation loops can be reduced until a desired amount of the graft 1100 resides within the bone tunnel. Tensioning the terminal ends 502, 504 of the suture length 500 can also secure the self-locking knot 1000 over the first through-hole 210. If desired, additional supplementary fixation (e.g., half hitch knots) can be applied to the self-locking knot 1000. To complete the procedure, the terminal ends of the ligament graft 1100 can be secured within the bone tunnel formed in the patient's tibia 106 in any of a variety of manners known in the art.

Figure 14A:
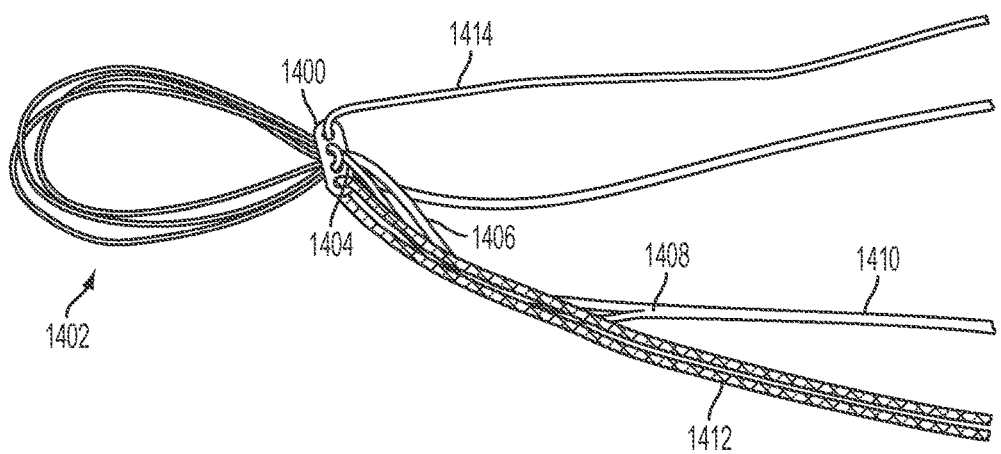
FIG. 14A is an illustration of one embodiment of an adjustable fixation implant and suture length having spliced-together opposed ends.
Figure 14B:
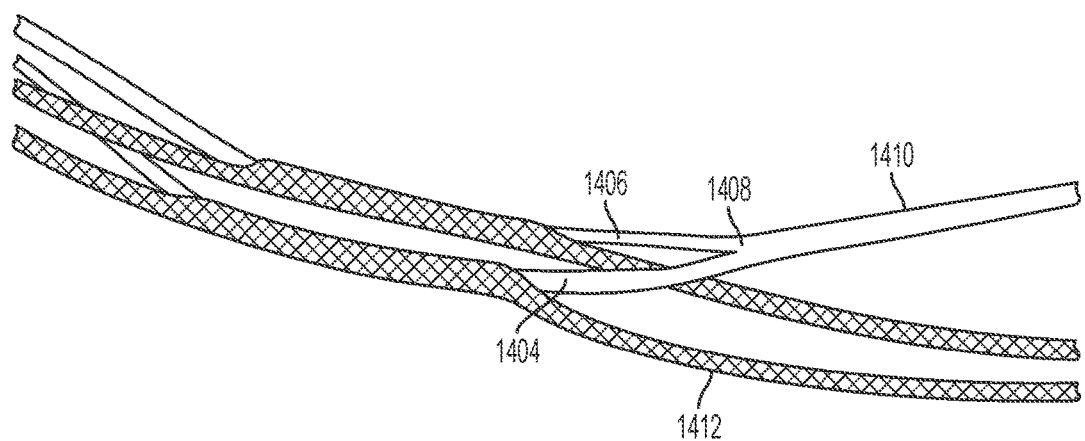
FIG. 14B is a close-view of the splice of FIG. 14A.

In certain embodiments, the terminal ends 502, 504 can be joined together to provide a user with a single suture strand for tensioning. This can be accomplished in a number of manners known in the art. In some embodiments, for example, the terminal ends 502, 504 can be spliced together to form a single terminal end, as shown in FIGS. 14A and 14B. FIG. 14A illustrates a body 1400, similar to the body 200 described above, that includes a plurality of fixation loops 1402 extending therefrom. The plurality of fixation loops 1402 can be similar to the fixation loops 602, 604, 802, and 804 described above, and can be formed by passing opposed ends 1404, 1406 of a suture length through the body 1400, as described above. In the illustrated embodiment, however, the opposed ends 1404, 1406 are joined to one another by a splice 1408, such that a user can tension the implant using a single length of suture 1410 extending from the splice. The ability to splice the terminal ends of the suture together is a unique feature made possible by the fact that, in the fixation devices and methods described herein, both terminal ends of a length of suture can be pulled simultaneously. By splicing the terminal ends together, a user need only hold a single strand of tightening suture, rather than two separate strands. This can serve to minimize implant complexity and possible confusion during use, as many different lengths of suture can be present (including, e.g., a shuttle suture 1412 and a rotation suture 1414 that can be threaded through outer through-holes of the body 1400, as described above).

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. A surgical implant, comprising:
   an elongate body having a longitudinal axis extending therealong and having first and second through-holes that are offset to a first side of the longitudinal axis and a third through-hole that is offset to a second side of the longitudinal axis and that is positioned between the first and second through-holes; and
   a suture length extending through the first, second, and third through-holes such that a self-looking knot is formed on a first side of the body, wherein the self-locking knot is positioned into at least one of the first and second through-holes and a plurality of suture loops are formed on a second side of the body opposite the first side.

2. The surgical implant of claim 1, wherein a diameter of each of the first and second through-holes is greater than a diameter of the third through-hole.

3. The surgical implant of claim 2, wherein a diameter of each of the first and second through-holes is about 1.6 mm.

4. The surgical implant of claim 1, wherein the self-locking knot is formed by first and second terminal ends of the suture length extending through the third through-hole and passing through a loop formed from a mid-portion of the suture length that extends from the first through-hole.

5. The surgical implant of claim 4, wherein the first and second terminal ends are spliced together.

6. The surgical implant of claim 1, further comprising a fourth through-hole and a fifth through-hole centered on the longitudinal axis, the first and second through-holes being positioned between the fourth and fifth through-holes.

7. The surgical implant of claim 6, wherein the second side of the body further includes cut-outs that extend along the longitudinal axis and are in communication with the fourth and fifth through-holes.

8. The surgical implant of claim 1, wherein a length of the body extending along the longitudinal axis is in a range of about 5 mm to about 20 mm, a width of the body extending along the first side or the second side of the body is in a range of about 2 mm to about 6 mm, and a thickness of the body extending between the first side and the second side of the body is in a range of about 1 mm to about 3 mm.

9. The surgical implant of claim 8, wherein the length of the body extending along the longitudinal axis is about 12 mm, the width of the body extending along the first side or the second side of the body is about 4.25 mm, and a thickness of the body extending between the first side and the second side of the body is about 2 mm.

10. The surgical implant of claim 1, wherein the body is formed from titanium.

11. A surgical implant, comprising:
   an elongate body having a longitudinal axis extending therealong and having first and second through-holes that are centered on the longitudinal axis and a third through-hole that is offset from the longitudinal axis and that is positioned between the first and second through-holes; and
   a suture length extending through the first, second, and third through-holes such that a self-locking knot is formed on a first side of the body, wherein the self-locking knot is positioned into at least one of the first and second through-holes and a plurality of suture bops are formed on a second side of the body opposite the first side.

* * * * *